Figure 1:
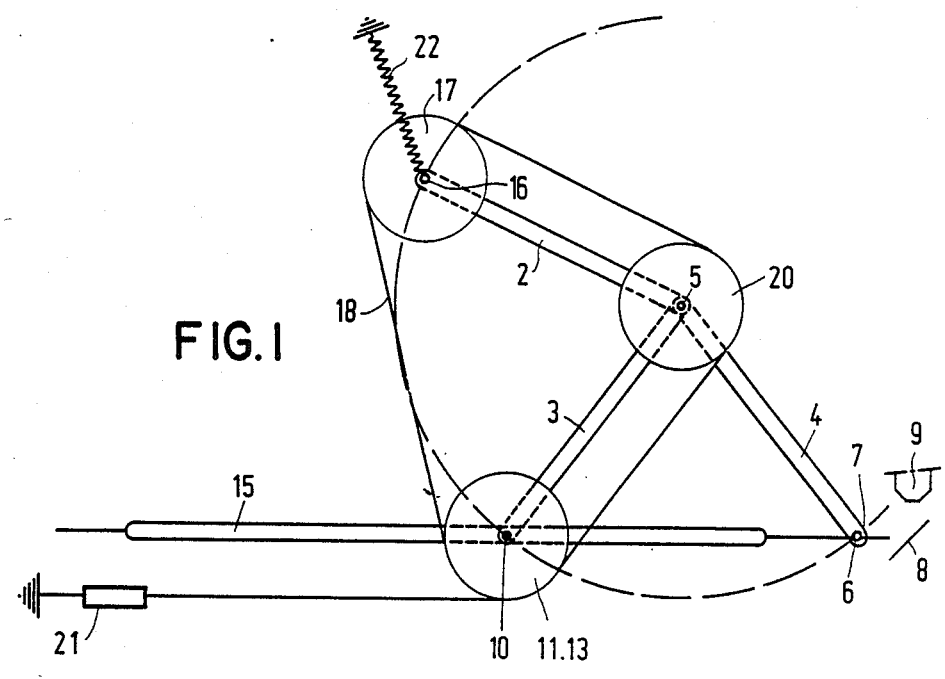

United States Patent [19]
Van Tol et al.

[11] Patent Number: 4,885,760
[45] Date of Patent: Dec. 5, 1989

[54] X-RAY ANALYSIS APPARATUS

[75] Inventors: Maurits W. Van Tol; Johannes H. A. Büter, both of Almelo, Netherlands

[73] Assignee: U.S. Philips Corporation, New York, N.Y.

[21] Appl. No.: 250,023

[22] Filed: Sep. 27, 1988

[30] Foreign Application Priority Data

Oct. 16, 1987 [NL] Netherlands ............... 8702475

[51] Int. Cl.$^4$ ............................... G01T 1/36
[52] U.S. Cl. ........................ 378/82; 378/70
[58] Field of Search .................. 378/70, 82-84

[56] References Cited

U.S. PATENT DOCUMENTS

| | | | |
|---|---|---|---|
| 3,445,653 | 5/1969 | Tomura | 378/82 |
| 3,546,453 | 12/1970 | Browning et al. | 378/83 |
| 3,566,111 | 2/1971 | Harm | 378/82 |
| 4,236,072 | 11/1980 | Schinkel et al. | 378/83 |
| 4,446,568 | 5/1984 | Williams et al. | 378/83 |
| 4,637,041 | 1/1987 | Brinkgreve et al. | 378/84 |
| 4,807,268 | 2/1989 | Wittry | 378/82 |

FOREIGN PATENT DOCUMENTS 2418372 10/1975 Fed. Rep. of Germany .

Primary Examiner—Craig E. Church
Assistant Examiner—John C. Freeman
Attorney, Agent, or Firm—Paul R. Miller

[57] ABSTRACT

Using a belt transmission and guide wheels, a linear drive for a detector arm of an X-ray monochromator is simply obtained, the angle between the detector arm and the crystal arm always being accurately equal to the angle between the crystal arm and the entrance slit.

3 Claims, 1 Drawing Sheet

X-RAY ANALYSIS APPARATUS

The invention relates to an X-ray analysis apparatus, comprising an X-ray source, a crystal holder and a detection device, the detection device being arranged on a first arm whilst the crystal holder is arranged on a second arm, the first and the second arm being pivotably coupled to one another, at a distance from the detection device and the crystal holder, respectively, in a pivot in which a third arm is pivotably coupled to the first and the second arm, the third arm also being pivotable, at a distance from the pivot, about a rigidly arranged pivot shaft, the end of the second arm supporting the crystal holder being displaceable along a straight path, the detection device, the crystal holder and the pivot shaft of the third arm being adjustable in different positions with respect to one another by pivoting the arms, so that the detection device, the crystal holder and the pivot shaft are positioned on a Rowland circle in the various positions.

An X-ray analysis apparatus of this kind is known from European patent application No. 0 118 965. In European patent application No. 0 118 965 an extensive analysis is given of the theory on which the construction of such an apparatus is based and also of the operation of such an apparatus; for the sake of brevity, therefore, for this theory and operation reference is made to the cited publication which is incorporated herein by way of reference.

In the known apparatus the end of the second arm which supports the crystal holder and which is remote from the pivot is guided, using a number of rollers, along a guide along which it is displaced by means of a drive motor. Furthermore, the end of the first arm which supports the detection device is displaceable along a guide between the end of the second arm which is remote from the pivot and the pivot by means of a number of rollers and a drive motor.

The displacement of the end of the second arm which supports the crystal holder is measured and converted into signals for activating the drive motor coupled to the first arm. The operation of the known apparatus is satisfactory, because very exact displacement of the various parts along the circumference of the Rowland circle can be realized. However, the construction of the apparatus is comparatively complex so that the apparatus is expensive.

The invention has for its object to realize an apparatus of the kind set forth which has a simple construction.

This can be achieved in accordance with the invention in that a wheel is rigidly connected to the detection device, in the pivot and near the crystal holder there being provided further, freely rotatable wheels whose diameters are the same, around the wheels there being guided a belt, one end of which is attached to the second arm at the area of the crystal holder, the belt being guided from this point of attachment successively along the wheel connected to the detection device, the wheel which is rotatable about the pivot shaft and the wheel which is arranged near the crystal holder, the other end of the belt being attached in a fixed point.

The coupling between the various displaceable parts is thus completely realized by means of simple mechanical means; it has been found in practice, that, despite this simple construction, a displacement of the mutually adjustable parts is obtained which is sufficiently accurate for many applications.

It is to be noted that U.S. Pat. No. 3,445,653 discloses an apparatus in which a crystal holder is arranged on a carrier which is slidably guided in two points along lines enclosing an angle with respect to one another. To this carrier there is coupled a second carrier which is slidable in a point along a guide. The second carrier comprises a member for transmitting X-rays in the direction of the crystal carrier. Both carriers comprise wheels around which there is guided a belt. Due to the various sliding guides used, this device is substantially more complex and more susceptible to deviations than the construction in accordance with the invention.

German Patent Specification No. 24.18.372 also discloses an X-ray analysis apparatus of the kind set forth in which a belt which is guided over different wheels is used for the correct displacement of the various parts with respect to one another. This construction, however, necessitates the use of wheels of different, accurately matched diameters which makes the manufacture of such a device more complex.

The invention will be described in detail hereinafter with reference to an embodiment of the construction in accordance with the invention which is diagrammatically shown in the accompanying Figures.

FIG. 1 diagrammatically shows the arrangement of the various parts of an apparatus in accordance with the invention.

Figure 2:
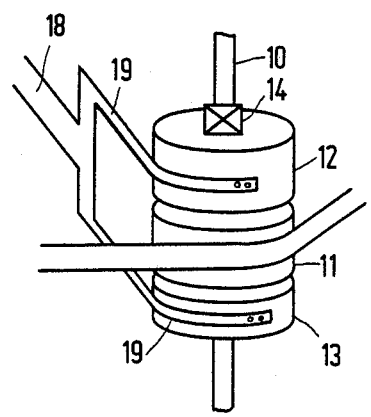

FIG. 2 is a diagrammatic perspective view of the guiding of the belt at the level of the crystal holder.

As appears from FIG. 1, the apparatus comprises three arms 2–4 whose facing ends are pivotably interconnected in a common pivot by means of a shaft 5.

The end of the arm 4 which is remote from the pivot 5 is pivotable coupled via a rigidly arranged pivot shaft 6 which extends parallel to the shaft 5, to the frame (not shown) of the apparatus in accordance with the invention. At the area of this shaft 6 there is arranged a shield 7 which is provided with a customary slit-shaped aperture for transmitting X-rays emerging from a specimen 8, which X-rays are incident on a crystal holder (not shown) which is secured to a shaft 10 about which the end of the arm 3 which is remote from the shaft 5 is rotatable. As is shown in detail in FIG. 2, the shaft 10 carries a wheel 11 which is arranged between two wheels 12 and 13 which have the same external diameter as the wheel 11. The shaft 10 is freely rotatable in the wheels 12 and 13 but is locked, using means not shown, against axial displacement with respect to these wheels.

At the upper side of the wheel 12 and the lower side of the wheel 13 there are secured guide blocks 14 which are slidable in slot-like guides 15 whose longitudinal axes extend in the prolongation of the direction of the X-rays transmitted by the shield 7.

A further wheel 17 is rotatably coupled to the end of the arm 2 which is remote from the shaft 5, using a shaft 16 which extends parallel to the shaft 5. A detection device (not shown) is coupled to the latter wheel.

As appears from FIG. 1, the distance between the shaft 5 and the shaft 6 equals the distance between the shaft 5 and the shaft 10 and the distance between the shaft 5 and the shaft 16.

On the two longitudinal guides 15 the frame of the apparatus is slidable; the wheels 12 and 13 are not rotatable with respect to this frame and extensions 19 which are secured to the end of a belt 18 are secured thereto in the manner shown in FIG. 2. As from this point of attachment at the area of the end of the arm 3 which supports the crystal holder the belt 18 extends in the direction of the wheel 17, continues along a part of the circumference of the wheel 17 and subsequently in the direction of a wheel 20 which is freely rotatable about the shaft 5, and from this wheel 20 to the wheel 11. The last part of the belt 18 extends parallel to the guides 15 and is secured, possibly via a tensioning device 21 (only diagrammatically shown), at a fixed point on the frame of the apparatus in accordance with the invention.

As is diagrammatically shown in FIG. 1, a tensile spring 22 is arranged between the end of the arm 2 which supports the wheel 17 and a fixed point on the frame of the apparatus, which spring can be used to keep the belt 18 taut.

The diameters of the various wheels 11, 17 and 20 are equal. Use is preferably made of a steel belt.

When the device is initially adjusted, it will be ensured, possibly by displacing the belt in its longitudinal direction by means of the tensioning device 21, that the distance between the entrance slit in the shield 7, arranged at the level of the shaft 6, and the shaft 10 is equal to the distance between the two shafts 10 and 16, so that the shafts 6, 10 and 16 will be situated on a so-called Rowland circle whose radius equals the distance between the shaft 5 and the shaft 10.

For re-adjustment of the apparatus there may be provided, for example, a drive member (not shown) which can be used to move the shaft 10 to and from along the guides 15. During this reciprocating movements of the shaft 10, the belt 18 will roll along the various wheels, thus displacing the shaft 16 supporting the detection device so that the entrance slit in the shield 7, the crystal holder and the detection device always remain suitably situated on a Rowland circle.

What is claimed is:

1. An X-ray analysis apparatus, comprising an X-ray source, a crystal holder and a detection device, the detection device being arranged on a first arm while the crystal holder is arranged on a second arm, the first and the second arm being pivotably coupled to one another at a first pivot point at a distance from the detection device and the crystal holder, respectively, a third arm pivotably coupled at said first pivot point to the first arm and the second arm, the third arm also being pivotable, at a distance from said first pivot point, about a rigidly arranged pivot shaft, an end of the second arm supporting the crystal holder being displaceable along a straight path; the detection device, the crystal holder and the pivot shaft of the third arm being adjustable in different positions with respect to one another by pivoting the first, second, and third arms, so that the detection device, the crystal holder and the pivot shaft are positioned on a Rowland circle; said X-ray analysis apparatus further characterized in that a wheel is rigidly connected to the detection device; the first pivot point and the second arm, near the crystal holder, each further comprise a freely rotatable wheel wherein the diameters of both freely rotatable wheels are the same; and around the freely rotatable wheels there being guided a belt, one end of the belt is attached to the second arm at the area of the crystal holder, the belt being guided from this area of attachment successively along the wheel connected to the detection device, the freely rotatable wheel of the first pivot point and the freely rotatable wheel of the second arm located near the crystal holder, an other end of the belt being attached to a fixed point.

2. An X-ray analysis apparatus as claimed in claim 1, characterized in that there are provided resilient means which pivot the first and the second arm with respect to one another in order to keep the belt taut.

3. An X-ray analysis apparatus as claimed in claim 1 or 2, characterized in that at the area of the crystal holder the one end of the belt comprises two attachment ends which are secured to two anchor wheels located between the wheel arranged near the crystal holder is arranged, the anchor wheels being locked against rotation.

* * * * *